United States Patent [19]

Heinz et al.

[11] Patent Number: 5,170,785
[45] Date of Patent: Dec. 15, 1992

[54] RATE VARYING PACEMAKER APPARATUS AND METHOD FOR DERIVING A PREFERRED ONE OF DIFFERENT PATIENT ACTIVITY CONTROL SIGNALS

[75] Inventors: Michael E. Heinz; Heinz P. Theres, both of Munich, Fed. Rep. of Germany

[73] Assignee: Dr. Eckhard Alt, Fed. Rep. of Germany

[21] Appl. No.: 808,790

[22] Filed: Jun. 17, 1991

Related U.S. Application Data

[63] Continuation of Ser. No. 518,511, May 2, 1990, Pat. No. 5,078,133.

[51] Int. Cl.⁵ .............................................. A61N 1/368
[52] U.S. Cl. ........................................... 128/419 PG
[58] Field of Search ............................... 128/419 PG

[56] References Cited

U.S. PATENT DOCUMENTS

| | | | |
|---|---|---|---|
| 4,091,817 | 5/1978 | Thaler | 128/419 PG |
| 4,300,566 | 11/1981 | Stindt et al. | 128/419 PG |
| 4,365,639 | 12/1982 | Goldreyer | 128/419 PG |
| 4,421,116 | 12/1982 | Markowitz | 128/419 PG |
| 4,694,830 | 9/1987 | Lekholm | 128/419 PG |
| 4,722,342 | 2/1988 | Amundson | 128/419 PG |
| 4,865,036 | 9/1989 | Chirife | 128/419 PG |
| 4,892,102 | 1/1990 | Astrinsky | 128/419 PG |
| 4,928,688 | 5/1990 | Mower | 128/419 PG |

*Primary Examiner*—William E. Kamm
*Attorney, Agent, or Firm*—Laurence R. Brown

[57] ABSTRACT

This pacing system relates to a rate varying cardiac pacemaker (1) for electricaly stimulating the heart of a pacemaker wearer. The electrical cardiogenic heart is detected on a multipolar single probe with the aid of individual electrodes (7 to 10). Bipolar electrodes in the atrium allows for detection of the intra-atrial actions (P-wave) as a first rate control signal for controlling the pacemaker in the atrially triggered ventricular pacing mode (VDD). A second rate control signal other than the P-wave correlating with patient activity is determined in parallel with the P-wave control signal. The two control signals are compared to decide if the intra atrial actions (P-waves) are appropriate control signals. Pace rate control is switched between the two signals in order to produce the most beneficial pacing mode to the patient, for example, VDD or VVI rate responsive modes. This control system can respond to unreliability or instabilities of the intrinsic atrial P-wave signal, for example, fibrillation and shift control to another appropriate rate responsive mode.

9 Claims, 4 Drawing Sheets

FIG.4a
FIG.4b
FIG.4c
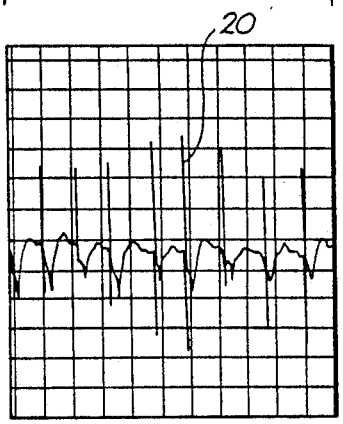
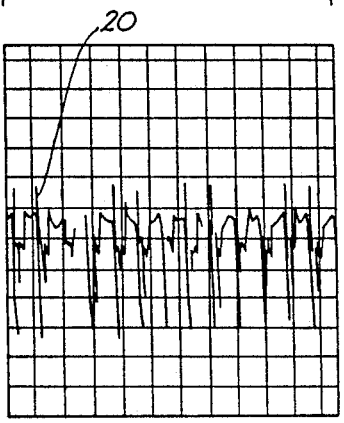
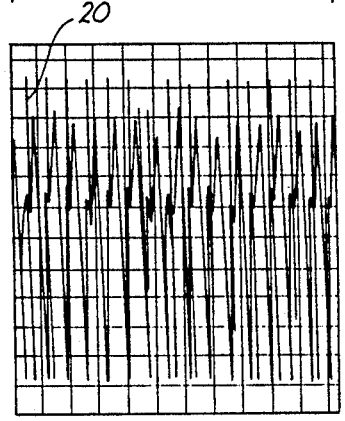
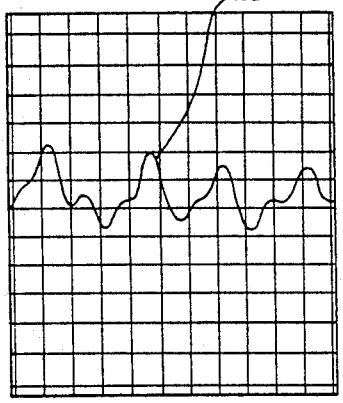
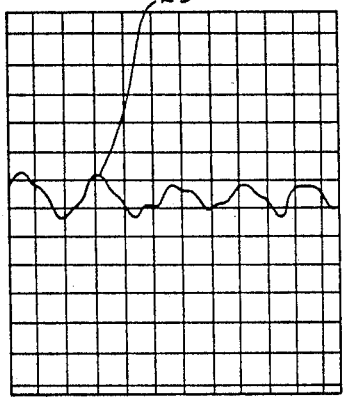
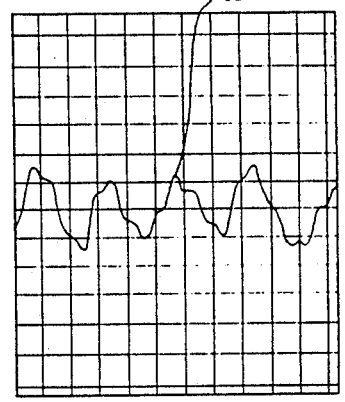
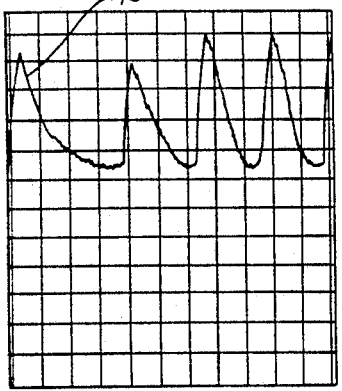
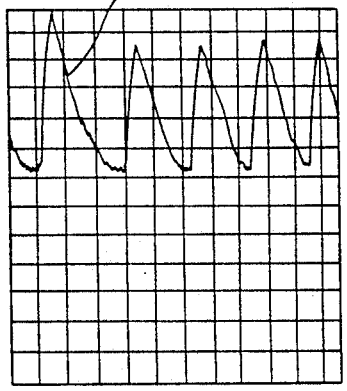
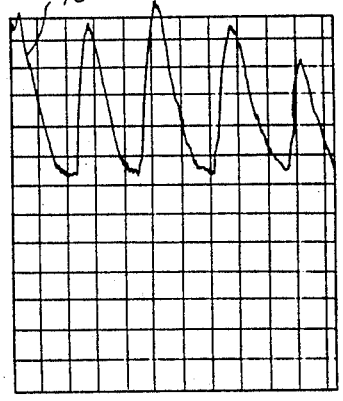

RATE VARYING PACEMAKER APPARATUS AND METHOD FOR DERIVING A PREFERRED ONE OF DIFFERENT PATIENT ACTIVITY CONTROL SIGNALS

This application is a continuation of application Ser. No. 07/518,511, filed May 2, 1990, now U.S. Pat. No. 5,078,133, Jan. 7, 1992.

TECHNICAL FIELD

The present invention relates to a cardiac pacemaker having a pulse generator for generating pacing pulses at a certain pacing rate, at least one pacing electrode disposed in the heart for receiving the pacing pulses, at least two measuring electrodes also disposed in the heart for detecting electrical parameters influenced by physiological quantities due to the patient's exercise, an evaluation circuit for the measuring electrode signals for determining a control signal adapted to the patient's exercise, and a control circuit for varying the pacing rate in accordance with the patient's exercise.

BACKGROUND ART

In the early years of pacemaker therapy, simple systems stimulating in the ventricle were used. This was due to the technical possibilities existing in the early sixties. Nevertheless, one soon recognized the value of an atrioventricular synchronization from a hemodynamic point of view. As early as 1963, Nathan described the application of an atrially triggered ventricle pacing system in the article "An implantable synchronized pacemaker for the long-term correction of complete heart block" in Circulation 23, 1963, pp. 682ff. This article made clear the advantages of rate control with simultaneous atrioventricular synchronization by detecting the atrial potential. Such pacemakers are advantageous in particular for patients with a complete AV block, i.e. if the stimulus conduction system in the heart is interrupted, that maintains the normal rhythm if the sinus node function still exists at the same time. Problems in reliably detecting the atrial signal led in past years to the development of an atrial screw electrode which is "screwed" into the atrial wall with a corkscrew-like spiral or the like. As of the mid seventies it became possible to detect the atrial signals with so-called VAT pacemakers and use them to trigger cardiac stimulation in clinical application.

However, the theoretical advantage of applying such atrially triggered VAT systems, which are known today as DDD systems or dual chamber systems, is opposed by considerable problems in practice. Firstly, the problem of firmly anchoring the electrodes in the atrium has not been satisfactorily solved, whether by screw electrodes or by inserting an electrode into the auricular appendix. The second problem relates to the instability of the atrial rhythm. A survey of this can be found in the book by E. Alt, "Schrittmachertherapie des Herzens," perimed Verlag, Erlangen (1988), pp . . . In many patients showing a disturbance of stimulus conductance, there are also disturbances in the stimulus formation. This means that, alongside an occasionally regular sinus rhythm, there may be fast atrial arrhythmias in the sense of atrial fibrillation or an atrial flutter, but that sinus node dysfunction may also express itself as an excessively slow sinus node function. This is referred to as a "brady-tachy syndrome" or, if the AV conduction is additionally disturbed, as binodal disease. In the case of fast atrial arrhythmias the ventricle is paced inadequately in the rhythm of the atrial arrhythmia; in the case of sinus node damage and a deficient rise in the sinus rate the pacing rate for the ventricle is too slow. Technical restrictions with respect to a reliable detection of the atrial signal and due to the limited expressive power of the atrial signal lead, for a considerable number of patients, to restrictions in the dual chamber or DDD systems used at present.

To avoid the problems with respect to an unstable anchoring of the atrial electrode, it has been proposed to provide a floating pair of electrodes in the atrium within one pacing lead. This concept was already presented in 1979 by Antonioli in the book "Cardiac pacing, PACE Symposium, Montreal," edited by C. Meere, in the article "A simple P-sensing ventricle stimulating lead driving a VAT generator." U.S. Pat. No. 4,313,442 (Knudson) describes a corresponding pacemaker which integrates the atrial pulse signals and adjusts a pacing rate in accordance with the integrated atrial signal. This method does not allow for direct synchronization between the atrial beat and the ventricular beat, but for an adaptation of the ventricular beat rate to the mean atrial rate.

The concept of detecting the atrial signals indirectly with a multipolar electrode corresponds to the technique, that has been practiced for many years in electrophysiology with transitory electrodes, of detecting the atrial signal with bipolar, quadripolar or six-pole floating electrodes that pass through the atrium by lying in the blood stream and are not secured by direct contact to the atrial wall. Two electrode points, i.e. a pair of electrodes in the ventricle and one or two pairs of electrodes in the atrium, are generally used within a common electrode body. More recent developments in electrode technology also allow for the application for thin multipolar electrodes whose diameter is only about 1.6 millimeters.

In the past it was not easy for the evaluating electronics of cardiac pacemakers, however, to detect these indirectly detected signals of the atrium with a floating electrode position. But now that microprocessor technology has made progress, it is possible to derive a control signal for ventricular pacing triggered in synchronism with the atrium within a DDD system by means of suitable input filters and input amplifiers as well as appropriate processing of the signal perceived indirectly in the atrium from floating electrode points within the blood stream.

When the problem of detecting the atrial signal with one electrode not in direct contact with the atrial wall is solved, however, one still has the problem of the instability of the cardiogenic atrial signal, which, as explained above, may be both too fast and too slow. Since the ventricular rate is adapted to this atrial signal in a classic DDD pacemaker, this may result in an inadequately fast or slow ventricular rate.

To obtain, independently of the atrial rate, a correct pacing rate in the ventricle that is adapted to the patient's exercise, various concepts for rate adaptive pacemakers have been proposed in the past.

Krasner describes in U.S. Pat. No. 3,593,718 a pacemaker in which the external thoracic impedance is measured, and the breathing rate detected therefrom and used for controlling the pacing rate.

Nappholz describes in U.S. Pat. No. 4,702,253 a pacemaker which provides a measuring current for measuring the impedance in order to use this impedance measurement to detect the breathing and use it for controlling the pacing rate.

Salo applies, according to U.S. Pat. No. 4,686,987, a similar impedance measuring method to determine the stroke volume of the right ventricle.

Lekholm also uses an impedance measurement for detecting the breathing rate according to U.S. Pat. No. 4,697,591.

In U.S. Pat. No. 4,694,830, the same inventor describes a pacemaker in which the particular impedance can be detected from the change in the stimulation voltage and the stimulation current during each generated stimulation pulse by division of the two stated values, and from the change therein the breathing rate can be indirectly detected, the latter then being used to control the pacing rate. However, this is only successful in cases in which pacing is effected only by the pacemaker. Cardiogenic heart beats cannot be used with this method for rate control and for detecting the breathing rate. This is an essential limitation of this system H. Strandberg, et al., in U.S. Pat. No. 4,757,815 controls pacing in accordance with amplitudes of QRS complex signals and varies the rate of the pacing pulses in response to shifting frequency of the respiration signal as acquired from fluctuations in the heart signal derived between a single electrode tip in the heart and a pacemaker housing. Respiration signals are thus subject to false variations such as by swinging the arms. Furthermore there is no fail-safe check of the respiration rate against any other sensed values to determine if it is an optimal control signal for pacing when starting or stopping strenuous exercise for example when the breathing rate is not necessarily an optimal indicator for pacing rate.

Most of the aforesaid systems use the detectable change in impedance to determine the breathing rate and use it for control of the pacing rate of the heart. An atrially synchronous control of the heart rate in the ventricle is not possible with such systems alone, since they have no suitable measures for detecting the atrial activity as well.

The invention is based on the problem of reliably controlling a cardiac pacemaker of the type in question with control signals for the pacing rate obtained from a selected optimum one of different cardiac activities with simple measuring technology and low operative effort and energy resources, and which furthermore provides the possibility of perceiving the signals of the atrium without an additional atrial electrode and using only one probe to the heart.

DISCLOSURE OF THE INVENTION

This problem is solved according to the invention by determining amplitude variations of the intracardiac cardiogenic signal due to the patient's breathing which are determined by the orientation of the vector of the cardiogenic stimulus current with respect to the axis of perception defined by the position of the measuring electrodes, and deriving therefrom the pacing control signal.

The invention thus makes use of the fact that the resultant of all cardiogenic electrical currents during depolarization of the myocardial cells, i.e. the so-called sum vector, has a determinating quantity and direction during the excitation process. If this vectorial electric stimulus, i.e. the intracardiac signal passing through the heart, is detected in terms of voltage and amplitude with the aid of a bipolar electrode, differential delays occur between the individual signals depending on the orientation of the bipolar electrode with respect to the vectorial electric field. If the two electrode points of the bipolar electrode are parallel to the vector, a bipolar signal is generated which exceeds the unipolar signal in terms of amplitude. If the bipolar electrode is disposed at right angles to the direction of conduction of the electrical stimulus, virtually isochronic potentials occur on the two individual electrodes, which subtract each other. Since the orientation of the vectorial electric field during the excitation process is determined by the instantaneous geometry of the heart, which is in turn a function of the breathing and thus of the position of the heart within the thorax in accordance with the diaphragmatic state, and the resulting change in the relation between the sum vector and the bipolar electrode position, one can determine the breathing by evaluating the amplitude variations of the bipolar intracardiac signal, and use it as a regulating variable for adjusting the pacing rate. The breathing, preferably the breathing rate, but also the breathing rate and breathing depth, can be used for this adjustment either alone or in conjuction with a further control parameter, whereby it is within the scope of the invention to use the breathing primarily or only supportively for this control. In the latter case the further control parameter is used primarily for adjusting the pacing rate. This takes account of the fact that cardiac pacemakers having several control parameters either detected by sensors or by detection of the natural atrial P wave are being increasingly used today because this can clearly increase the reliability of an adequate pacing rate.

The detection of the intracardiac signal can take place in the ventricle, the atrium or between the atrium and the ventricle. The amplitude variations are smallest upon detection in the ventricle, and greatest upon detection between the ventricle and the atrium. If only the electrical atrial signal is detected, an atrially triggered, a so-called VDD pacemaker with pacing of the ventricle can be used for pacing under control of the atrial P wave. The evaluation circuit of the pacemaker can then perform a comparison between the pacing rate calculated by the atrially triggered VDD method and the pacing rate calculated on the basis of the vectorial amplitude variation of the stimulus field and correlating with the breathing rate as a complimentary sensor control signal. After this comparison the evaluation circuit selects the suitable pacing rate for pacing the ventricle. An atrioventricular synchronization in accordance with the perception of atrial actions is also possible in the case of respiration triggered rate adaptive pacing.

In a pacemaker at least two electrode points are preferably disposed in the atrium and at least one electrode point in the ventricle. The evaluation circuit can then compare the perceived vectorial amplitude variations between various electrode points, thereby allowing for detection of the most favorably situated electrode points for determining the breathing individually.

In order to avoid interference influences from pacing pulses during detection of the electrical intracardiac signal, one picks up the intracardiac signal only a certain time after a pacing pulse has been provided ("blanking"). One can also determine the vectorial amplitude variations of the intracardiac signal by performing a signal correction for paced and perceived cardiogenic actions.

Upon detection of atrial instability such as atrial fibrillation one can also perform a strictly rate adaptive ventricular pacing (VVI) with the rate adaption in accordance with the vectorial amplitude variation of the intracardiac signal. The evaluation circuit can additionally perceive inadequate atrial tachyarrhythmias which are then not used for influencing the pacing rate. This would be the case for example if a high atrial rate is detected but the sensor signal indicates no state of physical exercise. In such a case the pacemaker automatically switches over to a new mode of operation in which rate adaptive ventricle pacing is performed in accordance with the vectorial amplitude variation of the intracardiac signal or in accordance with a further rate adaptive control parameter such as body activity detected by a motion sensor.

BRIEF DESCRIPTION OF THE DRAWINGS

Further features and advantages of invention can be found throughout the following description, drawings and claims.

The invention shall be explained in more detail in an exemplary embodiment with reference to the drawing, in which

FIGS. 4a, b, c show signal diagrams, picked up directly on a patient, of the electrical intracardiac signal, the breathing rate derived therefrom and the directly measured breathing of the patient;

THE PREFERRED EMBODIMENTS

Figure 1:
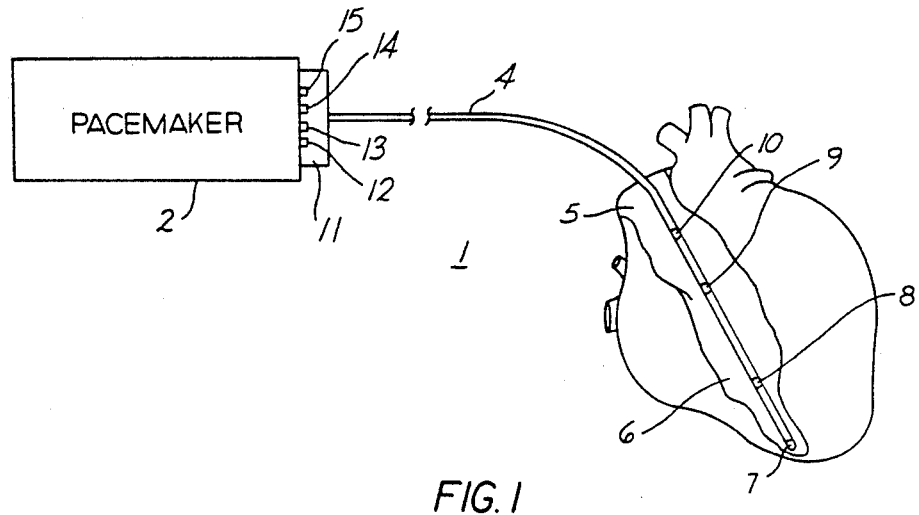
FIG. 1 shows a schematic view of an inventive cardiac pacemaker having an implantable pacemaker can and a probe connected to four individual electrodes and directed via the atrium into the right ventricle.
Figure 2:
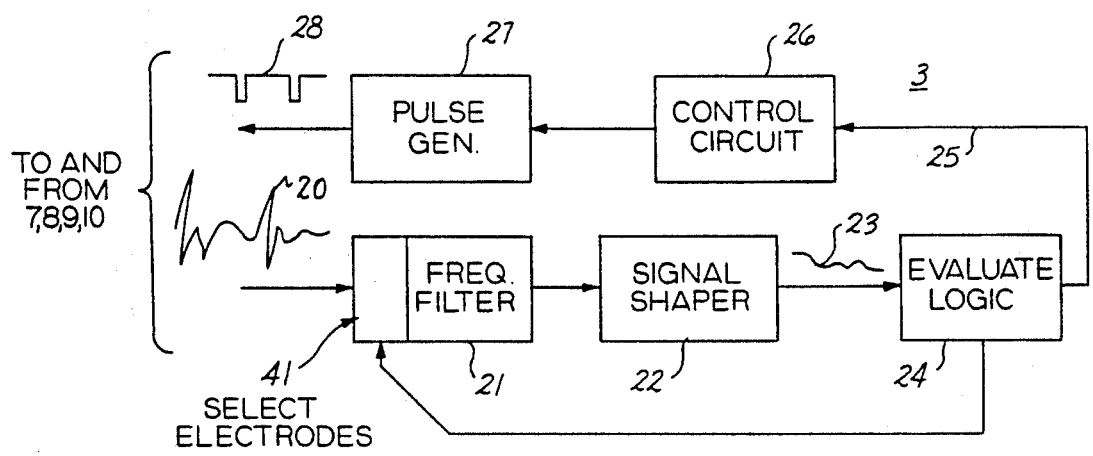
FIG. 2 shows a schematic block diagram to explain the basic function of the inventive pacemaker.

A pacemaker 1 comprises an implantable can 2 containing evaluation and control electronics 3 shown in FIG. 2, and a probe 4 connected to the pacemaker and introduced via right atrium 5 into ventricle 6 of a human heart. The probe has four electrodes 7, 8, 9 and 10, electrode 7 being situated at the tip of the probe, electrode 8 in the ventricle and electrodes 9 and 10 in atrium 5. Probe 4 is connected to the pacemaker can via a quadripolar connection 11 with terminals 12, 13, 14 and 15 indicated here only schematically.

The ventricle is paced e.g. in bipolar fashion via the two single electrodes 7 and 8 situated in the ventricle. The cardiogenic electrical signal during excitation is detected with the aid of two single electrodes, e.g. between electrodes 7 and 8 in the ventricle, between electrodes 9 and 10 in the atrium or perhaps between single electrode 8 in the ventricle and one of electrodes 9 or 10 in the atrium. This detection is strictly passive, requiring no energy supplied from the outside. The two single electrodes detect an electrical intracardiac signal which is indicated schematically as 20 in FIG. 2. This intracardiac signal is fed to a frequency filter 21 and thereafter to a signal shaper 22. The frequency filter has a frequency range adapted to the actually occurring breathing rates, and detects frequencies between 0.1 Hz and about 1 Hz with a peak at about 0.35 Hz, thus having a low pass function. Endogenic and exogenic signals are thereby extracted, e.g. the patient's heart rate or physical jolts. A preceding high pass of 0.1 Hz serves to stabilize the baseline. The intracardiac signal corresponds to an ECG signal with the known P- to T-wave components. Due to the low pass filtering, a signal 23 correlating with the breathing is directly applied to the output of the signal shaper; cf. also the second lines in FIGS. 4a to 4c. A control signal is derived from this signal in the known manner in an evaluation logic 24, said control signal being fed via a line 25 to a control circuit 26 for a pulse generator 27. Pulse generator 27 then provides pacing pulses 28 at a pacing rate adapted to the patient's particular exercise determined by the breathing. In the case of unipolar pacing of ventricle 6, pacing pulses 28 are provided to electrode 7 and to the pacemaker can as an opposite electrode; in the case of bipolar pacing they are provided to electrodes 7 and 7 in the ventricle.

Figure 3:
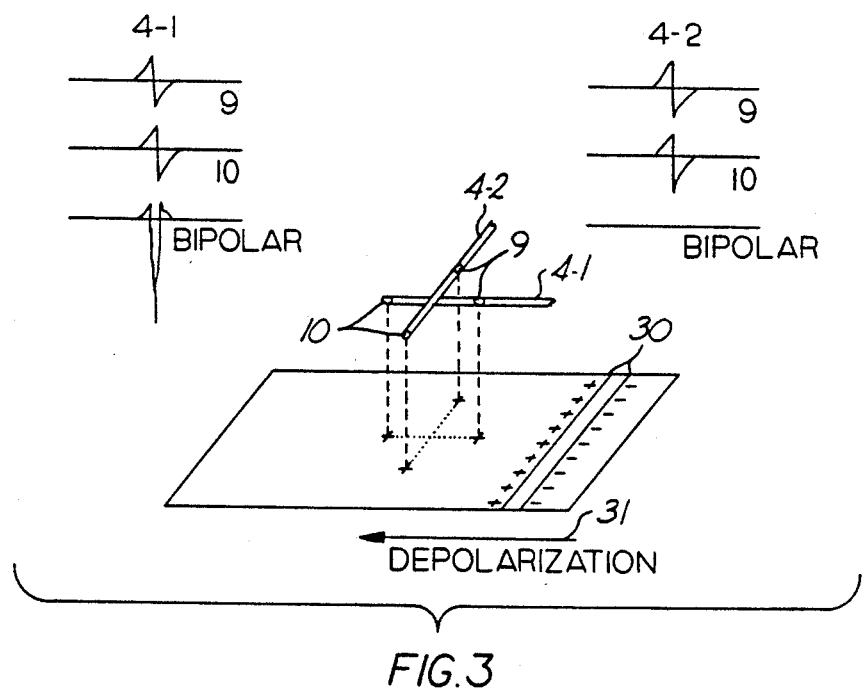
FIG. 3 shows a schematic view of the position of individual electrodes in the heart with respect to the wave front of the electrical intracardiac signal.

FIG. 3 shows a schematic view of the electrical processes within the heart in the case of bipolar perception, with two different positions of probe 4 within the atrium. These two positions are referred to as 4-1 and 4-2. The two electrodes are referred to schematically as 9 and 10. The electrical wave front following excitation of the heart can be represented as an arrangement of dipoles 30 which spread in accordance with arrow 31 in the direction of depolarization. In position 4-1 of the probe, i.e. when it is oriented parallel to the direction of depolarization, a positive potential first occurs at electrode 9 and is followed by a negative potential. Due to a time delay in the occurrence of this signal at electrode 10, caused by the transit time, a bipolar signal is generated which exceeds in terms of amplitude the particular signals detected in unipolar fashion; cf. the upper left signal representation in the figure. The bipolar perception acts in the manner of a differential amplification. If the probe is in position 4-2, i.e. at right angles to the direction of conduction of the stimulus front, isochronic potentials occur at electrodes 9 and 10 which subtract each other; cf. the upper right signal diagram in FIG. 3.

During operation of the pacemaker the position of probe 4 can be assumed to be relatively stationary, while the vector of the electrical wave front following excitation represented by arrow 31 changes with time, this change in time correlating with the breathing. Obviously, an evaluation of the amplitude variations of the signal detected in bipolar fashion results directly in a signal corresponding to the breathing.

FIGS. 4a, 4b and 4c shows original signal taken from patients.

FIG. 4a shows in the uppermost line intracardiac signal 20 which is detected in bipolar fashion in the atrium with an intrinsic sinus rhythm at a slow rate with the aid of single electrodes 9 and 10. Low pass filtering and (optional) signal shaping yield signal 23 determined in the second line, that is directly correlated with the breathing rate. The lowermost line shows a signal 40 corresponding to the directly measured breathing signal. One can see that signals 23 and 40 correlate very well with each other; there is a small apparent delay in the filtered signal relative to the directly measured breathing, which is due to the low pass filter.

FIG. 4b shows in the first line intracardiac signal 20 which was also detected with the aid of electrodes 9 and 10 in the atrium with pacing in the ventricle at 70 pacing pulses per minute. Signal 23 derived therefrom again correlates well with directly measured breathing signal 40.

In FIG. 4c intracardiac signal 20 was detected between the ventricle and the atrium. Signal 23 derived therefrom also correlates well with the directly measured breathing according to signal 40.

In order to select the particular most favorable signal 23, one can provide before frequency filter 21 a selection circuit 41 which is triggered by evaluation logic 24 and connects two selected electrodes with frequency filter 21. One can also integrate into this selection circuit 41 an extraction circuit which connects the selected electrodes with frequency filter 21 only a short time after a pacing pulse has been provided, thereby avoiding interference influences on the measurement by the relatively high energy of the pacing pulses.

Figure 5:
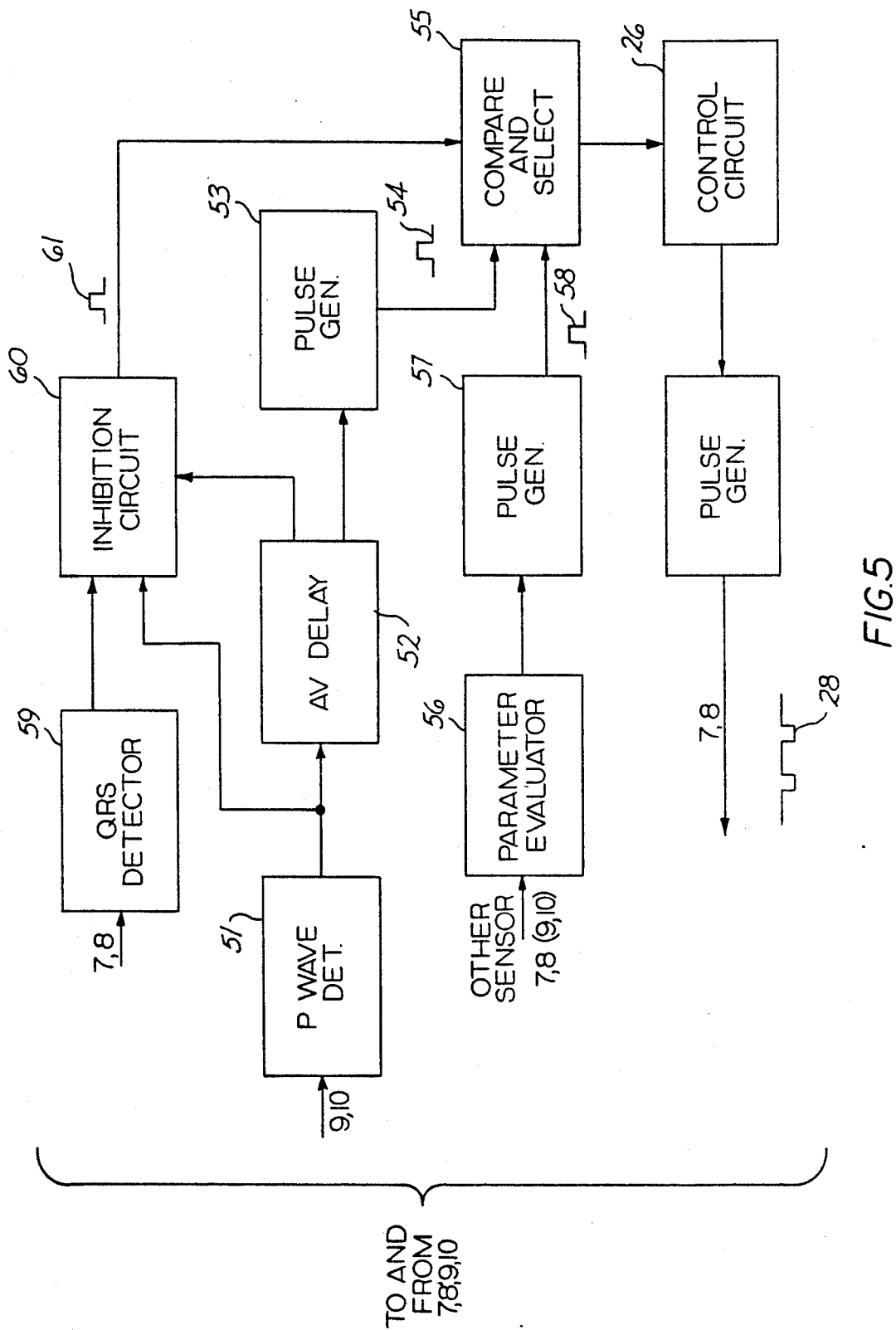
FIG. 5 shows a more detailed block diagram of an inventive pacemaker to explain further functions.

FIG. 5 shows a block diagram circuit for a portion of an atrially triggered pacemaker. Atrial electrodes 9 and 10 are connected to a P wave detector 51 which detects the P wave of the intracardiac signal. The output signal thereof is fed to a delay circuit 52 which provides a signal to a pulse generator 53 after about 150 milliseconds. This pulse generator provides a first pulsed control signal 54 to a comparator and selection circuit 55.

In a second branch of evaluation circuit 3' a rate adaptive control parameter is calculated by the above-described method in an evaluation circuit 56 from the signals of further electrodes, e.g. ventricular electrodes 7 and 8 or a ventricular electrode and an atrial electrode, and fed to a pulse generator 57. The latter provides a pulsed second control signal 58 to comparator and selection circuit 55, which in this case corresponds to the above-described control signal correlating with the breathing. It is also possible to evaluate the signals of another sensor in this second branch of the evaluation circuit and to calculate therefrom a rate adaptive control parameter which does not necessarily correlate with the breathing. Such control parameters may be determined e.g. from the pacemaker wearer's activity, the oxygen saturation or the temperature of the venous blood, etc.

Comparator and evaluation circuit 55 decides which of the control signals 54, 58 is passed on to control circuit 26 for the pulse generator, which then provides corresponding pacing signals 28 to the ventricular electrodes. In the atrially triggered pacemaker mode, first control signal 54 is usually passed on by comparator and evaluation circuit 55. Only when this signal shows no clear values or fails to correlate with an expected value according to the information of the second control signals 58 this is then used to control the pacing rate. Those conditions exist for example if the atrial rate is too slow (following newly developed virus mode disease) or too fast following atrial dyrythmias such as atrial flutter or atrial fibrillation. In this case the second control signal gains exclusive control over the pacing rate.

The ventricular signals provided by ventricular electrodes 7 and 8 are evaluated in a third branch of evaluation circuit 3'. The electrical signal is fed to a QRS detector 59 which detects the QRS wave following the P wave in the intracardiac signal. The detector signal is fed to a first input of an inhibition circuit 60 whose second input is connected to the output of P wave detector 51. Inhibition circuit 60 additionally receives from delay circuit 52 a pulse which characterizes the time delay of about 150 milliseconds preset there. Inhibition circuit 60 then provides a pulsed inhibition signal 61 to comparator and evaluation circuit 55 and blocks it when the output signal of QRS detector 59 is within the time span of 150 milliseconds preset by delay circuit 52. This therefore occurs only upon a cardiogenic beat, so that pacing is unnecessary in this case. The QRS wave usually follows the P wave after about 130 milliseconds in the case of cardiogenic rhythm.

Figure 6:
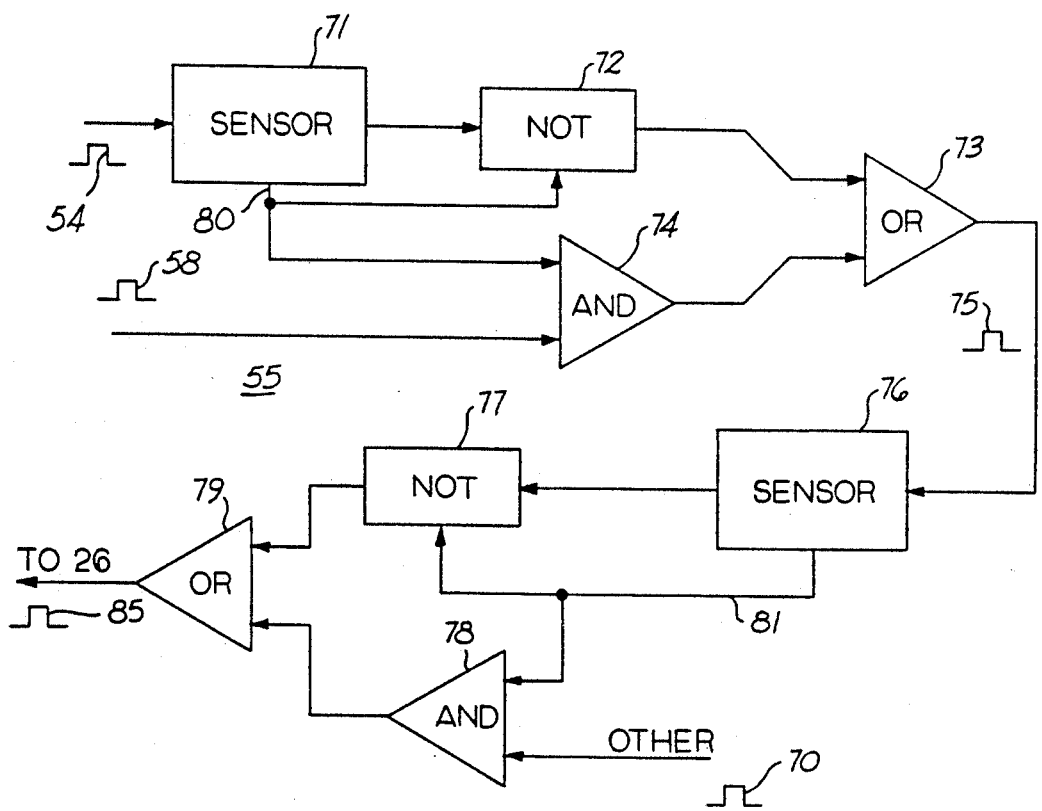
FIG. 6 is a block diagram of a typical preferred signal logic evaluation system, as provided by this invention.

The comparison and selection logic of block 55 is explained in more detail in connection with the logic diagram of FIG. 6. Thus the preferred pulse 54 dominates and goes to the pulse generator control circuit 26 provided sensor 71 shows that the signal is normal and proper. If not the lead 80 actuates NOT circuit 72 and blocks the signal 54 from OR circuit 73. Also the signal at 80 operates to pass through AND circuit 74 the alternative signal 58, which proceeds through OR circuit 73 in place of signal 54. The sensor 71 for example could detect the presence of dysrythmia such as fibrillation or flutter.

Thus signal pulse 75 is the survivor of signals 54 and 58 which proceeds to the output control circuit 26 via NOT circuit 77 and OR circuit 79 if pulse analysis sensor 76 indicates that the pulse train is good and thus does not inhibit the signal at NOT circuit 77 over lead 81. A further alternative pulse 70 can be selected if neither pulses 54 or 58 are available via AND circuit 78 in the presence of a signal on lead 81, when pulse 75 is unsatisfactory. Thus, the final pulse 85 is the survivor of pulses 75 and 70 as processed by OR circuit 79.

Thus, this invention provides a pacemaker evaluation system that may select a preferred one of several signal choices available at the series of electrodes in the heart or other sensing means for pacing. This for example provides for selection of the best available atrial P-wave signal 54 or vector signal 58 provided by floating electrodes in the right ventricle and atrium in the presence of heart activity. Such heart activity such as exercise can change the character of the signals acting upon the electrodes by displacement of the heart tissue in a way that cchanges the vector relationship of the signals and floating electrodes, as set forth in FIG. 3. But, this invention also prevents the deterioration of sensed signals at a particular electrode set that could cause erratic pacing from causing disfunction by switching to a different mode of operation of the pacemaker such as one responding to different heart activity measuring means. For example if sensor 76 finds arrythmia present in an atrial signal, it can substitute the signal 70 produced from some other sensing means or control pulse sequence.

Thus the method of operation provided by this invention comprises generating pacing pulses for stimulation of the heart via an electrode implanted in the heart, varying the pacing pulses in response to exercise activity of the patient in a normal P-wave triggered mode of operation and switching over the pacing mode in response to sensed abnormal P-wave conditions under control of a sensor. This can be achieved by means of selection of a proper subset of electrodes disposed in the heart for control purposes in accordance with a preferred embodiment of the invention.

In particular VDD pacing by means of floating electrode means in the atrium for detection of the atrial signal is a preferred manner of normal pacer operation, and in this mode of operation the vector signals are processed to produce a more reliable sensing of real rather than perceived atrial conditions in accordance with this invention. However a second order of improvement under emergency conditions is afforded by this invention, for example by sensing very high atrial rates indicating false atrial tachycardia to compare with a different heart condition sensor to correctly choose another mode or sensor that can better control the pacing rate.

Having therefore advanced the state of the art those features of novelty descriptive of the nature and spirit of the invention are defined with particularity in the following claims.

We claim:

1. A rate varying pacemaker, comprising in combination, means for generating pacing pulses a single pacing probe having stimulation electrode means positioned therealong for stimulation of the ventricle of a patient and measuring electrode means for producing atrial signals, means for deriving a first P-wave rate control signal indicative of intrinsic atrial activity at the measuring electrode means, means for controlling pacing pulses in response to the first P-wave rate, control signal means for deriving a second rate control signal different from the atrial P-wave reflecting activity level of the patient, and means for comparing the rate control signals with a predetermined rate control signal condition deriving as a preferred signal, the second rate control signal for controlling the pacing rate in the presence of pulse, faster than said predetermined condition.

2. The pacemaker of claim 1 further comprising pacing means for pacing both the atrium and the ventricle, and for pacing the ventricle as a function of the second rate control signal when said predetermined condition comprises atrial instability.

3. The pacemaker of claim 1 wherein additional measuring electrodes are located on the probe for positioning in the right ventricle for deriving said second rate control signal.

4. The pacemaker of claim 1 including means responsive to the second rate control signal for effecting a rate adaptive ventricular pacing mode signal (VVI-R).

5. The pacemaker control system of claim 1, wherein the single pacing probe further includes more than one pair of bipolar measuring alectrodes for positioning respectively within the ventricle and atrium to detect different vector signals, and the means for comparing the two signals derives a preferred one of the vector signals for controlling the pacing rate with signals from one of the pairs of bipolar electrodes presenting a vector signal of greatest amplitude.

6. The pacemaker of claim 1 wherein the probe electrode means comprises bipolar electrodes.

7. The pacemaker of claim 1 further comprising electrode means operable to detect a set of vectorial intracardiac signals of various amplitudes as said second rate control signal, and including means for sensing a preferred vectorial signal after a short delay period following a pacing impulse to avoid interference influences from high pacing energy.

8. The pacemaker of claim 1 wherein said means for deriving a second rate control signal comprises a sensor of activity of the patient representing a rate adaptive control parameter other than breathing.

9. The method of operating pacemakers producing pacing pulses comprising the steps of: producing pacing pulses in said pacemaker, sensing one condition of heart activity as an intracardiac electrical atrial P-wave signal, controlling the pacing pulses as a function of said P-wave signal as an initial preferred signal, determining abnormally fast atrial signals representative of atrial futter or fibrillation, producing a second control signal representative of the activities of a patient other than breathing, and changing control of the pacing pulses to vary the pacing signals as a function of the second control signal upon determination of said abnormally fast atrial signals.

* * * * *